(12) United States Patent
Rahn et al.

(10) Patent No.: US 7,542,597 B2
(45) Date of Patent: Jun. 2, 2009

(54) METHOD FOR CORRECTION OF RELATIVE OBJECT-DETECTOR MOTION BETWEEN SUCCESSIVE VIEWS

(75) Inventors: John Richard Rahn, Sammamish, WA (US); Alan C. Nelson, Gig Harbor, WA (US)

(73) Assignee: VisionGate, Inc., Gig Harbor, WA (US)

( * ) Notice: Subject to any disclaimer, the term of this patent is extended or adjusted under 35 U.S.C. 154(b) by 238 days.

(21) Appl. No.: 11/558,593

(22) Filed: Nov. 10, 2006

(65) Prior Publication Data

US 2007/0071357 A1 Mar. 29, 2007

Related U.S. Application Data (60) Division of application No. 10/876,328, filed on Jun. 24, 2004, now Pat. No. 7,260,253, which is a continuation-in-part of application No. 10/126,026, filed on Apr. 19, 2002, now Pat. No. 7,197,355.

(51) Int. Cl.
G06K 9/00 (2006.01)
G06K 9/40 (2006.01)
G06K 9/64 (2006.01)
G06K 9/32 (2006.01)

(52) U.S. Cl. .................. 382/133; 382/275; 382/278; 382/294

(58) Field of Classification Search .................. None
See application file for complete search history.

(56) References Cited

U.S. PATENT DOCUMENTS

| | | |
|---|---|---|
| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeles, Jr. |
| 3,748,468 A | 7/1973 | Hartman |
| 3,833,762 A | 9/1974 | Gudmundsen |
| 3,960,449 A | 6/1976 | Carleton |
| 3,999,047 A | 12/1976 | Green |

(Continued)

FOREIGN PATENT DOCUMENTS

WO        WO0111341 A2        2/2002

(Continued)

OTHER PUBLICATIONS

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

(Continued)

*Primary Examiner*—Charles Kim
(74) *Attorney, Agent, or Firm*—Citadel Patent Law; George A. Leone (57) ABSTRACT

An apparatus and method for correction of relative object-detector motion between successive views during optical tomographic imaging in three dimensions. An object of interest is illuminated to produce an image. A lateral offset correction value is determined for the image. An axial offset correction value is determined for the image. The lateral offset correction value and the axial offset correction value are applied to the image to produce a corrected file image.

16 Claims, 10 Drawing Sheets

U.S. PATENT DOCUMENTS

| | | | |
|---|---|---|---|
| 4,175,860 A | 11/1979 | Bacus | |
| 4,183,623 A | 1/1980 | Haines | |
| 4,200,353 A | 4/1980 | Hoffman | |
| 4,293,221 A | 10/1981 | Kay | |
| 4,360,885 A | 11/1982 | Edgar | |
| 4,714,345 A | 12/1987 | Schrader | |
| 4,858,128 A | 8/1989 | Nowak | |
| 4,873,653 A | 10/1989 | Grosskopf | |
| 4,891,829 A | 1/1990 | Deckman | |
| 5,141,609 A | 8/1992 | Sweedler | |
| 5,148,502 A | 9/1992 | Tsujiuchi | |
| 5,189,518 A | 2/1993 | Nishida | |
| 5,281,517 A | 1/1994 | Bacus | |
| 5,308,990 A | 5/1994 | Takahashi | |
| 5,312,535 A | 5/1994 | Waska | |
| 5,321,501 A | 6/1994 | Swanson | |
| 5,402,460 A | 3/1995 | Johnson | |
| 5,548,395 A | 8/1996 | Kosaka | |
| 5,550,892 A | 8/1996 | Katsevich | |
| 5,552,605 A * | 9/1996 | Arata | 250/363.04 |
| 5,668,887 A | 9/1997 | Parker | |
| 5,673,300 A | 9/1997 | Reckwerdt | |
| 5,680,484 A | 10/1997 | Ohyama | |
| 5,710,429 A | 1/1998 | Alfano | |
| 5,741,411 A | 4/1998 | Yeung | |
| 5,757,981 A | 5/1998 | Kawakubo | |
| 5,760,901 A | 6/1998 | Hill | |
| 5,760,951 A | 6/1998 | Dixon | |
| 5,828,408 A | 10/1998 | Mottin | |
| 5,848,123 A | 12/1998 | Strommer | |
| 5,878,103 A | 3/1999 | Sauer | |
| 5,880,838 A | 3/1999 | Marx | |
| 5,909,476 A | 6/1999 | Cheng | |
| 5,915,048 A | 6/1999 | Hill | |
| 5,987,158 A | 11/1999 | Meyer | |
| 6,005,617 A | 12/1999 | Shimamoto | |
| 6,026,174 A | 2/2000 | Palcic | |
| 6,038,067 A | 3/2000 | George | |
| 6,047,080 A | 4/2000 | Chen | |
| 6,072,624 A | 6/2000 | Dixon | |
| 6,078,681 A | 6/2000 | Silver | |
| 6,091,983 A | 7/2000 | Alfano | |
| 6,130,958 A | 10/2000 | Rohler | |
| 6,165,734 A | 12/2000 | Garini | |
| 6,192,144 B1 | 2/2001 | Holz | |
| 6,201,628 B1 | 3/2001 | Basiji | |
| 6,211,955 B1 | 4/2001 | Basiji | |
| 6,215,587 B1 | 4/2001 | Alfano | |
| 6,239,871 B1 | 5/2001 | Gilby | |
| 6,248,988 B1 | 6/2001 | Krantz | |
| 6,249,341 B1 | 6/2001 | Basiji | |
| 6,251,586 B1 | 6/2001 | Mulshine | |
| 6,251,615 B1 | 6/2001 | Oberhardt | |
| 6,252,979 B1 | 6/2001 | Lee | |
| 6,312,914 B1 | 11/2001 | Kardos | |
| 6,388,809 B1 | 5/2002 | MacAulay | |
| 6,452,179 B1 | 9/2002 | Coates | |
| 6,519,355 B2 | 2/2003 | Nelson | |
| 6,522,775 B2 | 2/2003 | Nelson | |
| 6,529,614 B1 | 3/2003 | Chao | |
| 6,591,003 B2 | 7/2003 | Chu | |
| 6,608,682 B2 | 8/2003 | Ortyn et al. | |
| 6,636,623 B2 | 10/2003 | Nelson | |
| 6,640,014 B1 | 10/2003 | Price | |
| 6,697,508 B2 | 2/2004 | Nelson | |
| 6,741,730 B2 | 5/2004 | Rahn | |
| 6,775,399 B1 | 8/2004 | Jiang | |
| 6,868,177 B1 | 3/2005 | Camahort | |
| 6,904,163 B1 * | 6/2005 | Fujimura et al. | 382/131 |
| 6,944,322 B2 | 9/2005 | Johnson et al. | |
| 7,141,773 B2 | 11/2006 | Kaplan et al. | |
| 7,197,355 B2 | 3/2007 | Nelson | |
| 2001/0012069 A1 | 8/2001 | Derndinger | |
| 2002/0122167 A1 | 9/2002 | Riley et al. | |
| 2002/0161534 A1 | 10/2002 | Adler | |
| 2003/0210760 A1 | 11/2003 | Nelson | |
| 2003/0222197 A1 | 12/2003 | Reese | |
| 2004/0001618 A1 | 1/2004 | Johnson | |
| 2004/0008515 A1 | 1/2004 | Brown | |
| 2004/0076319 A1 | 4/2004 | Fauver | |
| 2004/0228520 A1 | 11/2004 | Dresser | |
| 2005/0006595 A1 | 1/2005 | Goodwin et al. | |
| 2005/0085721 A1 | 4/2005 | Fauver et al. | |

FOREIGN PATENT DOCUMENTS

| | | |
|---|---|---|
| WO | WO0218537 A2 | 3/2002 |
| WO | WO0235474 A1 | 5/2002 |
| WO | WO 02/095476 | 11/2002 |

OTHER PUBLICATIONS

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1998:41:504-509.

George, JS et al., "Virtual Pinhole Confocal Microscope," Physics Division Progress Report, www.lanl.gov/p/pdfs/papp_pinhole.pdf, (1999-2000).

Pawley, JB, Handbook of Biological Confocal Microscopy, Plenum Press, NY, 479-490 (1995).

Reymond and Pickett-Heaps (1983), entitled "A Routine Flat Embedding Method for Electron Microscopy of Microorganisms Allowing Selection and Precisley Oriented Sectioning of Single Cells by Light Microscopy," Journal of Microscopy, vol. 130 Pt. 1 Apr. 1983 pp. 79-84.

Nicewarner-Peña et al., "Submicrometer Metallic Barcodes," Science 294 137 (2001).

Schmitz et al, "Performance Characteristics of a Silicon Photodiode (SiPD) Based Instrument for Fast Functional Optical Tomography," SUNY Downstate Medicial Center, Brooklyn, NY 11203.

Schmitz et al., "Instrument for Real-Time Dynamic Optical Tomography,"SUNY Downstate Medicial Center, Brooklyn, NY 11203.

Polymicro Technologies "Square Flexible Fused Silica Capillary Tubing," (2003) www.polymicro.com.

Shannon, The Art and Science of Optical Design, (1977) University of Arizona, Cambridge University Press, Fig. 4.12 and Fig. 4.13.

Fauver et al., Development of Micro-Optical Projection Tomography for 3D Analysis of Single Cells, Image Acquisition and Processing XI. Edited by Conchello, Jose-Angel; Cogswell, Carol J.; Wilson, Tony. Proceedings of the SPIE, vol. 5324, pp. 171-181 (2004).

Kikuchi, S. et al., "Three-dimensional computed tomography for optical microscopes," Optics Communications 107 (1994) 432-444.

Kikuchi, S. et al., "Three-dimensional microscopic computed tomography based on general Radon transform for optical imaging systems," Optics Communications 123 (1996) 725-733.

Matula, P. et al. "Precise 3D image alignment in micro-axial tomography," Journal of Microscopy, vol. 209 Pt. 2 (Feb. 2003) pp. 126-142.

Ong, SH, Development of an imaging flow cytometer. Anal Quant Cytol Histol 9(5)pp. 375-382 1987.

Gilbert, P, "Iterative Methods for the Three dimensional Reconstruction of an Object from Projections," Journal of Theoretical Biology 36pp. 105-117 1972.

Oppenheim, BE, "More Accurate Algorithms for Iterative 3 dimensional Reconstruction," IEEE Transactions on Nuclear Science NS-21pp. 72-77 1974.

Singer, JR, Grunbaum, FA Kohn, P, and Zubelli, JP, "Image Reconstruction of the Interior of Bodies that Diffuse Radiation," Science 248(4958)pp. 990-993 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237 2001.

Bellman, SH, Bender, R. Gordon, R, and Rowe, JE, "Art is Science being A Defense of Algebraic Reconstruction Techniques for Three dimensional Electron Microscopy," Journal of Theoretical Biology 32pp. 205-216 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947-1957 1989 #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241 1995 #4389.

Hampel, U and Freyer, R, "Fast Image Reconstruction for Optical Absorption Tomography in Media with Radially Symmetric Boundaries", Medical Physics 25 (1)pp. 92-101 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-931998.

Herman, G, Image Reconstruction from Projections: The Fundamentals of Computerized Tomography, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525 TDI, Time Delay and Integration Sensor, Jan. 12, 2001.

Farichild Imaging, Preliminary Data Sheet CCD582 TDI, Time Delay and Integration Sensor, Jan. 18, 2000.

Shapiro, HM, Practical Flow Cytometry, 3rd ed., Wiley-Liss, 1995.

HJ Tiziani and MI Uhde, Three-dimensional analysis by a microlens array confocal arrangements (Applied Optics 33 567 [1994]).

Bayat, S, Le Duc, G, Porra, L, Berruyer, G, Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282 (R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992 Institute of Physics Ser. No. 130 Kenway, PB, et al. (eds.), Manchester, UK, Aug. 31-Sep. 4, 1992 pp. 559-566.

Defrise, M, Clark, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197 1988.

Kinney, JH and Nichols, MC, "X-ray Tomographic Microscopy (XTM) Using Synchrotron Ratiation", Annu. Rev. Mater, Sci. 22pp. 121-152 1992.

Taguchi, K and Aradate, H, "Algorithm for Image Reconstruction in Multi-slice Helical CT", Medical Physics 25(4) pp. 550-561 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105 2000.

Sharpe, J, Ahlgren, U et al., "Optical Projection Tomography as a Tool for 3D Microscopy and Gene Expression Studies," Science, vol. 296 pp. 541-545 Apr. 19, 2002.

Sharpe, J, review, "Optical Projection Tomography as a New Tool for Studying Embryo Anatomy," J. Anat. (2003), pp. 175-181.

RH Anderson, "Close-up imaging of documents and displays with lens arrays," AppliedOptics 18 477 (1979).

Kak, A.C. and Slaney, M., Principles of Computerized Tomographic Imaging, IEEE Press, New York, 1988.

E.G. Steward, Fourier Optics: An Introduction, 2nd ed. (Halsted Press, New York, 1987).

A. Klug and J.L. Finch, "Structure of viruses of the papilloma-polyma type," J. Mol. Biol., vol. 37 p. 1 (1968).

A. Klug, "Image analysis and reconstruction in the electron microscopy of biological macromolecules," Chem. Scripta, vol. 14 p. 245 (1978).

T.C. Wedberg and J.J. Stamnes, "Recent results in optical diffraction microtomography," Meas. Sci. Technol., vol. 7 p. 414 (1996).

Y. Li, et al., "Comparison of analog and digital Fourier transforms in medical image analysis," J. Biomed. Optics, vol. 7 p. 255 (2002).

Y. Xu et al., "Three-dimensional diffuse optical tomography of bones and joints," J. Biomed. Optics, vol. 7 p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements,"Cytometry, vol. 2 No. 5 pp. 327-336 (1982).

M. Rozycka, et al., "Optical Diffraction as a Tool for Semiautomatic, Quantitative Analysis of Tissue Specimens," Cytometry, vol. 2, No. 4 pp. 244-248 (1982).

W. H. Press et al., Numerical Recipes in C (New York: Cambridge University Press, 1988).

Almedia and Fuji, Fourier transform differences and averaged simularities in diatoms, Applied Optics, vol. 18 No. 10 pp. 1663-1667 (1979).

Smolinska and Dawidowicz, "Extraction of common of different part from optical images," Institute of Physics, Warsaw Technical University, 222-223.

Miles, CP, Jaggard, DL, "The Use of Optical Fourier Transforms to Diagnose Pleomorphism, Size and Chromatin Clumping in Nuclear Models," Anal Quant Cytol Histol vol. 3 No. 2 pp. 149-156 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78:435-449.

Edelmann, P. et al., Correlation of chromatic shifts and focal depth in Spectral Precision Distance Microscopy measured by Micro Axial Tomography, Optical Biopsies and Microscopic Techniques III, Sep. 1999, SPIE vol. 3568, pp. 89-95.

* cited by examiner

METHOD FOR CORRECTION OF RELATIVE OBJECT-DETECTOR MOTION BETWEEN SUCCESSIVE VIEWS

RELATED APPLICATIONS

This application is a divisional of U.S. patent application Ser. No. 10/876,328, filed Jun. 24, 2004, of Rahn et al., entitled "Method for Correction of Relative Object-Detector Motion Between Successive Views," issued Aug. 21, 2007 as U.S. Pat. No. 7,260,253 which is incorporated herein by this reference, and is in turn a continuation-in-part of U.S. patent application Ser. No. 10/126,026, filed Apr. 19, 2002, of Nelson, entitled "Variable Motion Optical Tomography of Small Objects," issued Mar. 27, 2007 as U.S. Pat. No. 7,197,355, which is also incorporated herein by this reference.

FIELD OF THE INVENTION

Computer Program Listing Appendix

A total of two compact discs as Copy 1 and Copy 2, created Mar. 4, 2009, each containing the following files is attached as the computer program listing appendix and are incorporated herein by this reference. Both compact discs, Copy 1 and Copy 2, are identical and contain the text of an example of source code for implementing one embodiment of the method of the invention for registration correction. CD Copy 1 and CD Copy 2 both contain the identical file named "60100USD1_USAN11558593," of size: 25,228 bytes and were both created on Mar. 4, 2009.

The executable file (regcorr.exe) is built from two header files (rrahn.h and regcorr.h) and four C++ files (fileinfo.cp, nr-fft.cpp, multiplycomplexvalues.cpp, and regcorr2.cpp), linked by project regcorr.ide. The project was compiled by Borland C++ 5.01, set for "Win32 Console" mode, and using the static class library framework. The executable file size is roughly 60 kB. (Programs, "regcorr.exe" and "regcorr_no-_lateral.exe," differ only in whether they provide the option of calculating the lateral offset and writing it to a text file. Both programs can also skip the calculations and instead read the offsets from a text file.)

The present invention relates to imaging and, more particularly, to detection of and correction for relative object-detector motion in an imaging system where, typically, successive views from different positions are acquired, each view representing a two-dimensional projection or pseudo-projection of the three-dimensional object.

BACKGROUND OF THE INVENTION

An optical projection tomographic microscope (OPTM) is suitable for high-resolution imaging of a microscopic object, such as a biological cell and its nucleus, which are embedded in a fluid medium and contained within a microcapillary tube having inner and outer diameters of 40 microns and 150 microns, respectively. An OPTM employs a plurality of views, each acquired by rotating the object and its containment vessel about an axis perpendicular to the optical axis and parallel to the axis of the microcapillary tube. A camera, having a CCD image sensor composed of an M×N array of pixels, captures the light after it has passed through the object and the imaging optics, which produce a magnified image of the field of view (FOV) on the CCD. Since each view is taken from a different perspective, the content of each view will differ from the others.

Owing to the extremely small sizes of the components, it can be quite difficult to position the axis of rotation (typically coincident with the central axis of the microcapillary tube) in the center of the detector's FOV. It is further very difficult to hold the microcapillary tube stationary while rotating it. In addition, the cell itself may move along the tube axis in between views. As a result, each view, which is already altered due to the tube rotation, can in addition be subject to translations both axial (parallel to the microcapillary axis) and lateral (perpendicular to the optical axis and to the tube axis). These lateral translations are in addition to those already present for objects that are not on the rotation axis.

In order to obtain an accurate 3D reconstruction, whether through filtered backprojection or other means, it is therefore necessary to correct for the axial motion and for that portion of the lateral motion that is not due to the changing perspective from one view to another. It is further necessary to determine where in the detector FOV the axis of rotation is located.

U.S. Pat. No. 4,858,128, to Nowak describes a method where consecutive scenes are correlated with one another, first in one axis and then, independently, in the other axis. The location of the maximum value for the two correlations determines the required offset for the two axes. The method described fails to provide means for distinguishing the "natural" lateral translation, due to the change in perspective, from the "erroneous" lateral translation, due to translation of the microcapillary tube. The Nowak patent teaches, "it may be useful to estimate such background component of the signal and to subtract the estimate from the image data."

William H. Press et al., *Numerical Recipes in C: The Art of Scientific Computing,* Cambridge University Press; 2nd edition (Jan. 1, 1993) describe means for implementing, via a computer program, the techniques of cross-correlation between two arrays of data using fast Fourier transforms (FFTs). In brief, the cross-correlation of two data arrays (such as image data) can be obtained by applying an FFT to each array, multiplying one of the resulting arrays by the complex conjugate of the other, and applying an inverse FFT to the result.

In order to overcome current shortcomings in the state of the art, it is an objective of the present invention to provide a method for finding the location of the central axis of a microcapillary tube for each view in a multi-view imaging system. It is a further objective of the invention to provide a method for detecting relative object-detector motion between successive views in a multi-view imaging system. It is a further objective of the invention to provide a method for correcting image data to remove errors due to object motion during image data collection. It is a still further objective of the invention to provide an imaging system of a type producing a plurality of X-Y data matrices representing projection or pseudo-projection views of an object for subsequent tomographic reconstruction of axial slices of the object. The detected motion may be removed by suitably shifting later data to align it with earlier data, or vice versa.

SUMMARY OF THE INVENTION

The present invention provides an apparatus and method for correction of relative object-detector motion between successive views during optical tomographic imaging in three dimensions. An object of interest is illuminated to produce an image. A lateral offset correction value is determined for the image. An axial offset correction value is determined for the image. The lateral offset correction value and the axial offset correction value are applied to the image to produce a corrected file image.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings described hereinbelow.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited. Although the present invention may be employed in other types of imaging systems, such as, for example, X-ray computed tomography (CT) imaging, for concreteness of description the following disclosure is directed toward the invention in the environment of an optical projection tomographic microscopy (OPTM) system.

In the discussion that follows, the following assumptions are used when providing numerical examples:
1. Each image consists of an array, 640 pixels wide by 480 pixels high;
2. Each pixel contains a single 8-bit (gray level 0 to 255) brightness value;
3. With reference to an OPTM using a microcapillary tube, the tube axis is parallel to the shorter axis (480 pixels);
4. With reference to an OPTM using a microcapillary tube, the tube wall separation is 530 pixels;
5. The number of bins used in finding the lateral offset (B1) is 20;
6. The number of bins used in finding the axial offset (B2) is 2;
7. The array is zero-padded to 1024 by 1024 pixels.

It is to be understood that these numerical values are for illustrative purposes only; other numerical values may be employed without detracting from the nature of the invention.

Figure 1:
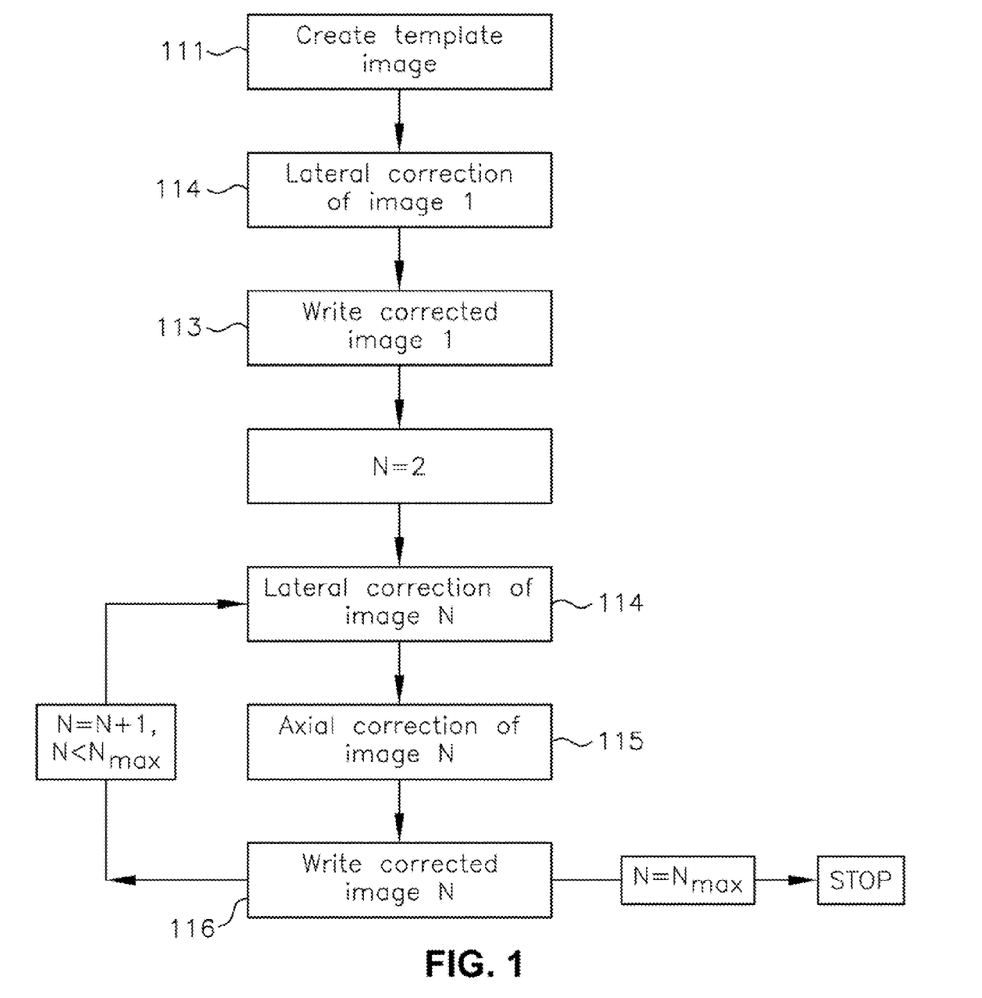
FIG. 1 is a functional block diagram of an example embodiment of a method for correction of relative object-detector motion between successive views constructed in accordance with the teachings of the present invention.

Referring now to FIG. 1, a functional block diagram of an example embodiment of a method for correction of relative object-detector motion between successive views constructed in accordance with the teachings of the present invention is shown. In the example embodiment, an altered copy of each image is generated, in which the brightest pixels are reassigned a brightness level of zero, while all other pixels retain the same brightness as in the initial image. A two-dimensional (2D) FFT of this thresholded image is then multiplied, pixel-by-pixel, with the complex conjugate of the 2D FFT of a reference image. The brightness of the resulting array is then summed along each line parallel to the axis of the microcapillary tube (to be referred to henceforth as the Y axis) to develop a one-dimensional (1D) array containing information about the brightness pattern in the direction (to be referred to henceforth as the X-axis) perpendicular to the optical axis and to the microcapillary axis. A 1D FFT is then applied, and the location of the maximum is determined. The location determines the amount of offset to be applied along the X-axis in order to bring the image of the microcapillary tube's center axis to its desired position in the image.

The reference image takes advantage of the constancy of the separation between the walls of the microcapillary tube, and consists of two maximally bright lines separated by the known amount found in the acquired images; the rest of the reference image has zero brightness. The tube walls appear only faintly in the pseudo-projection images, as the refractive indices of the tube walls are matched with materials inside the tube and between the tube and the slide/coverslip assembly. The effect of the histogram operation is to enhance the contrast between the tube walls and the rest of the image. Using the predetermined tube wall separation, in combination with the known number of pixels along the X-axis of the image, makes it possible to distinguish the movement of the tube itself from the movement of the objects within the tube, due to the rotation of the tube and the consequent perspective change. By cross-correlating the two images based on a constant feature, our method minimizes the possibility of tracking the movements of changing features within the cell.

A cross-correlation method is used to determine the amount of the axial offset from the Y-axis. To do so, a copy of the original image is again thresholded, but using different criteria for determining which pixels are reset to zero brightness. A 2D FFT is applied to this image, and multiplied, pixel-by-pixel, with the complex conjugate of the 2D FFT of the thresholded image derived from the immediately preceding view. A 2D FFT is applied to the result, and the X-axis offset is determined as the maximum in the cross-correlation function along the line that corresponds to the difference in the lateral correction of the current image with that of the previous image. This is a distinction from previous methods, in that the X-axis is constrained by the Y-axis offset; it is not found independently of the Y-axis offset.

Unlike the lateral correction, the axial correction is an iterative process and thus is subject to cumulative errors. The axial cross-correlation functions effectively, however, as long as the change in perspective between consecutive images is not too large; this corresponds to small angular increments in the rotation. By keeping the angular increment small, the spatial content does not vary by much, allowing the cross-correlation to track similar features in each image. Since the angular increment also determines the lateral resolution of the 3D tomographic reconstruction, the requirement that the angular increment be kept small to allow the cross-correlation to work well is not an onerous one.

Briefly stated, this embodiment of the present invention removes the effects of axial and lateral movement by the microcapillary tube by suitably shifting subsequent images to align them with previous images, or vice versa. Cross-correlation methods are used to find the offset on the lateral axis, then on the tube axis, with the restriction that the peak correlation for the axial movement must come after the determination of the lateral movement.

The first step 111 is to generate the binary template image. Two white lines having, for example, a grayscale level of 65,535, are created at their ideal positions. Each line has a length of 480 pixels, running parallel to the short image dimension. The locations of the two lines are determined by the long image dimension (640 pixels) and the tube wall separation, empirically determined as 530 pixels. The first line is located at line 0 and the second line is located at line 530. In this embodiment, the size of the template image may be expanded from 640×480 to 1024×1024 to provide zero-padding in both dimensions; however, this action is not essential to the invention.

A 2D FFT is performed on the template image so that real and imaginary components are saved in alternating indices of the resulting array. Thus, for a zero-padded array, the array size is 2048×1024. The template image is now in a form ready for use.

At step 114 the lateral offset is found. In step 114, the image is thresholded in order to black out the background pixels, and then cross-correlated with the binary image of two bright lines. Images of interest are subject to the lateral offset determination 114. The difference between the lateral correction 114 of the current image and that of the previous image is also saved for use in the axial correction 115.

Figure 2:
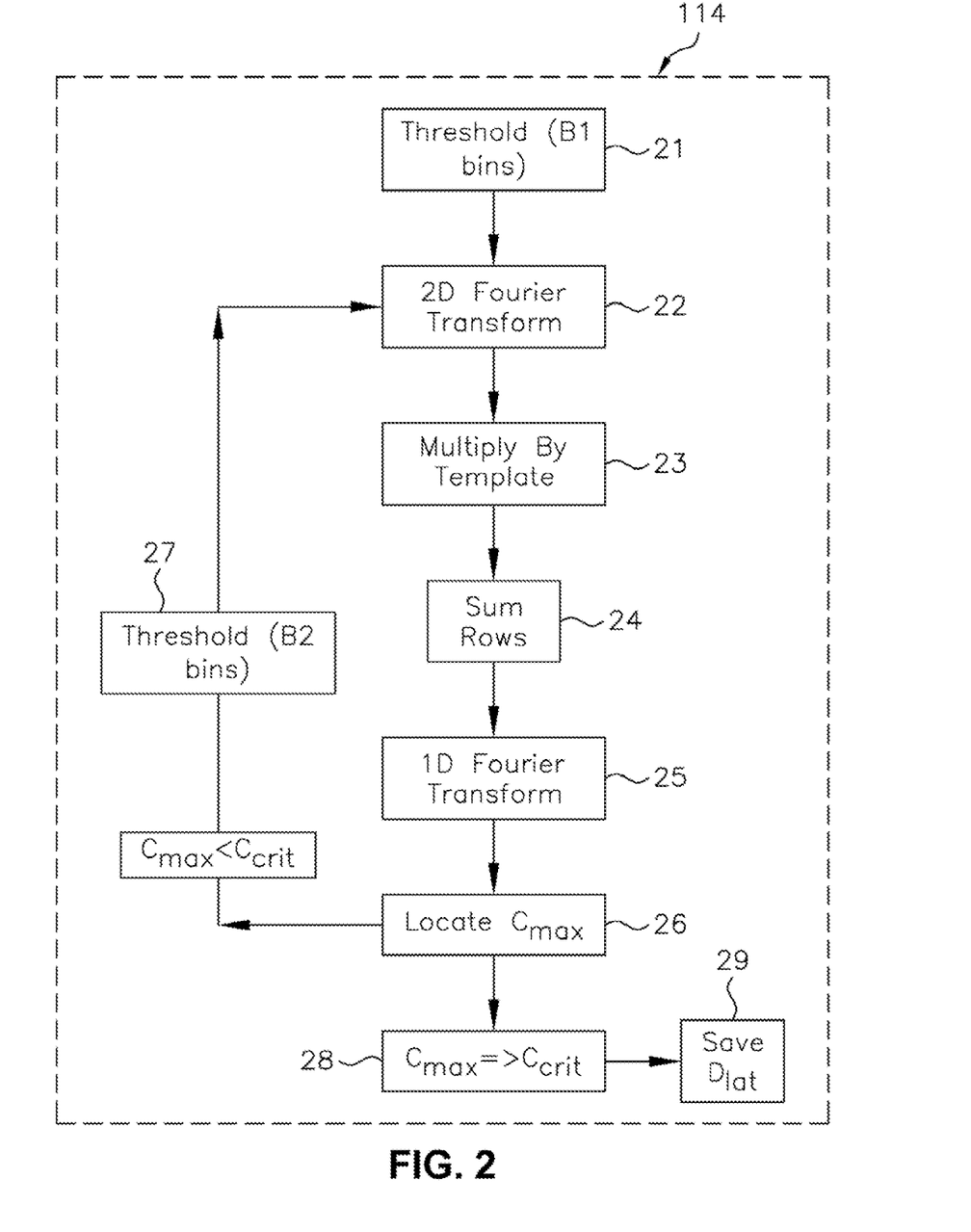
FIG. 2 is a functional block diagram of a lateral correction portion of an imaging system employing the example embodiment described in FIG. 1.

Referring now to FIG. 2, a functional block diagram of a lateral correction portion of an imaging system employing the example embodiment described in FIG. 1 is shown. The steps involved in finding the lateral offset 114 include constructing a grayscale histogram of the image, where the number of bins (B1) may be set at any integer value from 2 to 255. For the present example, it is assumed that B1=20. The bin with the greatest number of pixels is found (except the first bin, corresponding to the darkest pixels), and all pixels in the original image having that bin's grayscale value or higher are set equal to zero in a copy of the original image. The effect of this procedure 21 is to remove the background pixels from further consideration in order to produce a thresholded image.

As an example, suppose the input image has minimum and maximum grayscale values of 31 and 190, respectively, so that each bin has a width of eight gray levels [(1+190+31)/20=8]. Now further suppose that peak in the histogram occurs at bin #16 (i.e., gray levels from 151 to 158). Then the thresholded image will be similar to the original image, except that all pixels with an initial gray level greater than 150 now have a gray level of zero.

Figure 4A:
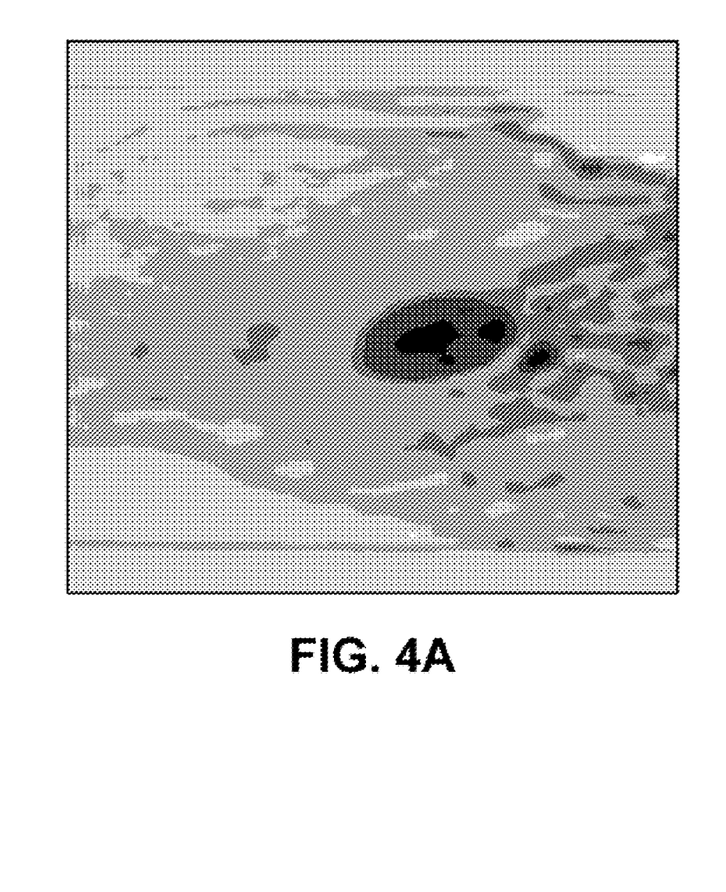
FIG. 4A depicts an image of a cell prior to thresholding operations that are employed in one example of the method of the present invention.
Figure 4B:
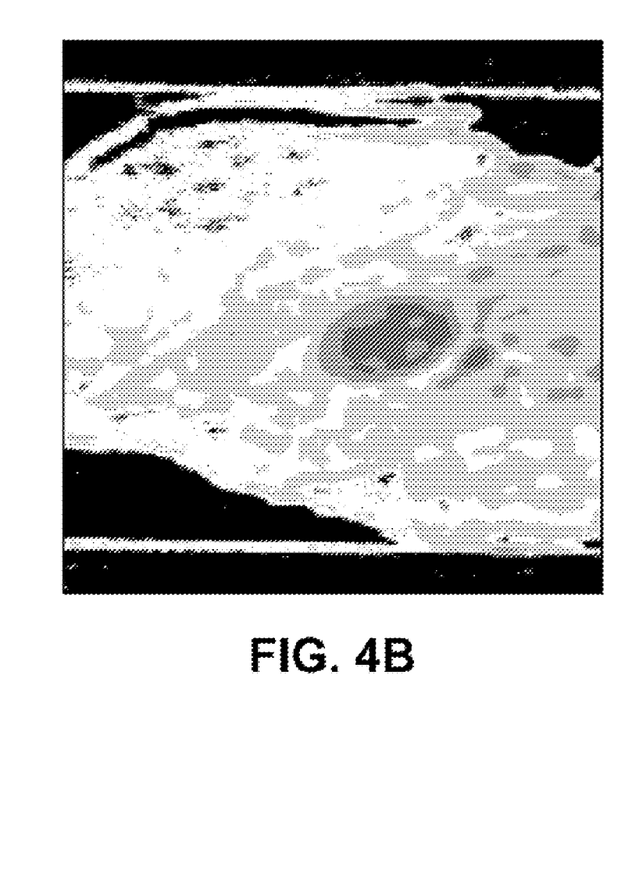
FIG. 4B depicts the result of applying thresholding operations that are employed in one example of the method of the present invention to the image shown in FIG. 4A.
Figure 4C:
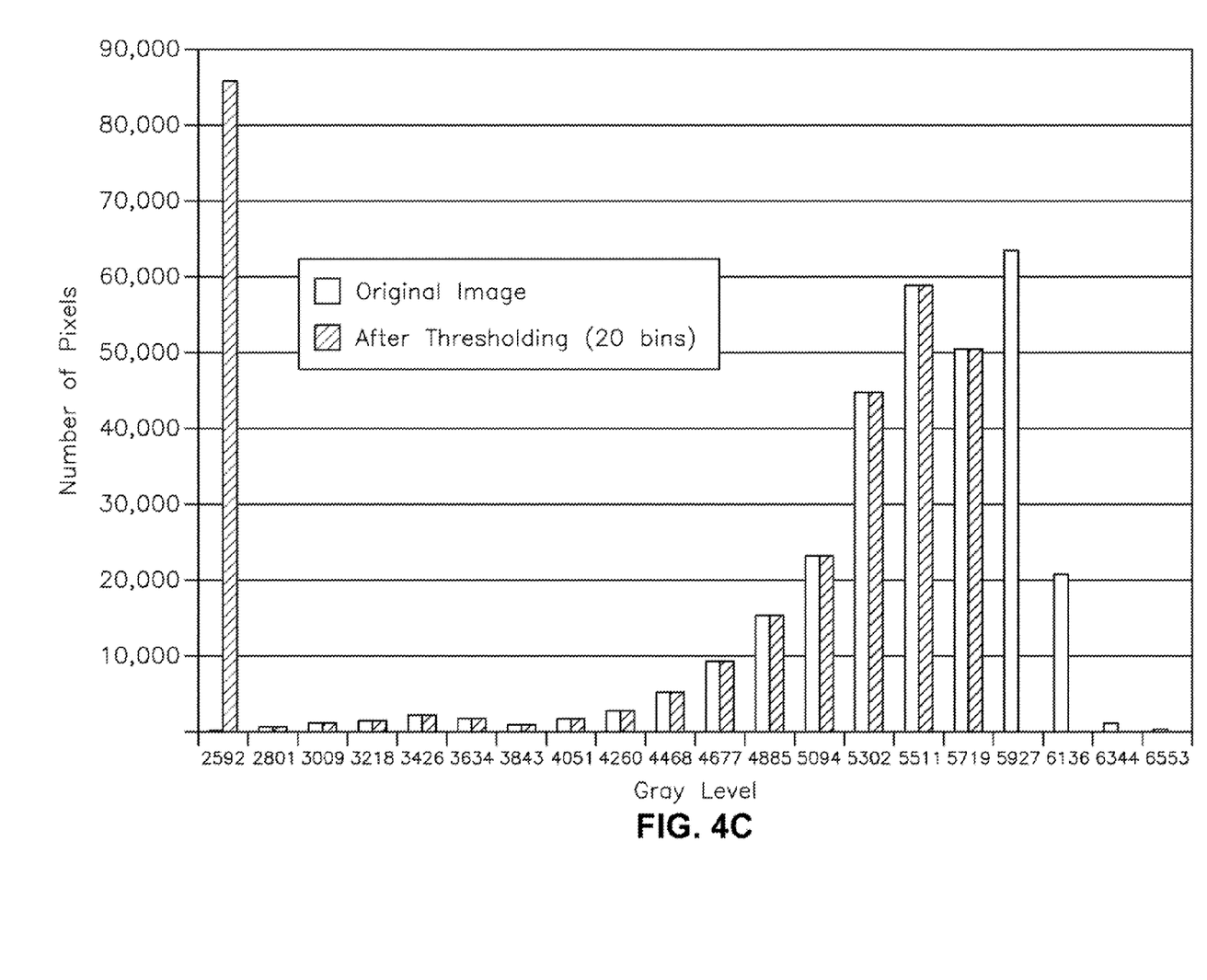
FIG. 4C illustrates a histogram showing brightness distributions of the images shown in FIGS. 4A-4B.

FIGS. 4A-4C illustrate the effect of applying these steps 21 to an image. A visual comparison of an original image to a segmented image may be made with reference to FIG. 4A, which shows an example of a cell image prior to segmentation and thresholding, and then to FIG. 4B which shows an example of a segmented and thresholded cell image corresponding to the original image of FIG. 4A. FIG. 4C is a histogram of an example image showing a comparison of the gray levels of the original image and the image after thresholding is applied.

A 2D FFT is applied to the thresholded image 22, and its Fourier transform is multiplied 23 by the complex conjugate of the Fourier transform of the template image. The resulting array is summed 24 along and each of the 640 rows to compute a new array, which is Fourier transformed (in 1D) 25 to find the cross-correlation of the rows of the thresholded image and the reference image. The maximum value of the 1D array is located 26 and evaluated 28. The position of the maximum is designated as $D_{LAT}$ and its magnitude is designated as $C_{MAX}$.

The necessary offset is determined by the difference between $D_{LAT}$ and its ideal position of 55 [(640−530)/2=55]. Thus, for example, if $D_{LAT}$=63, then an upward shift of 8 pixels is necessary (63−55=8), while if $D_{LAT}$=41, then a downward shift of 14 pixels (55−41=14) is required.

The procedure 114 is repeated for all images in the data set. Note that each image is referenced to the same template, so there is no cumulative error. To assist in the axial correction, $D_{LAT}$ is saved 29 for each image.

Figure 3:
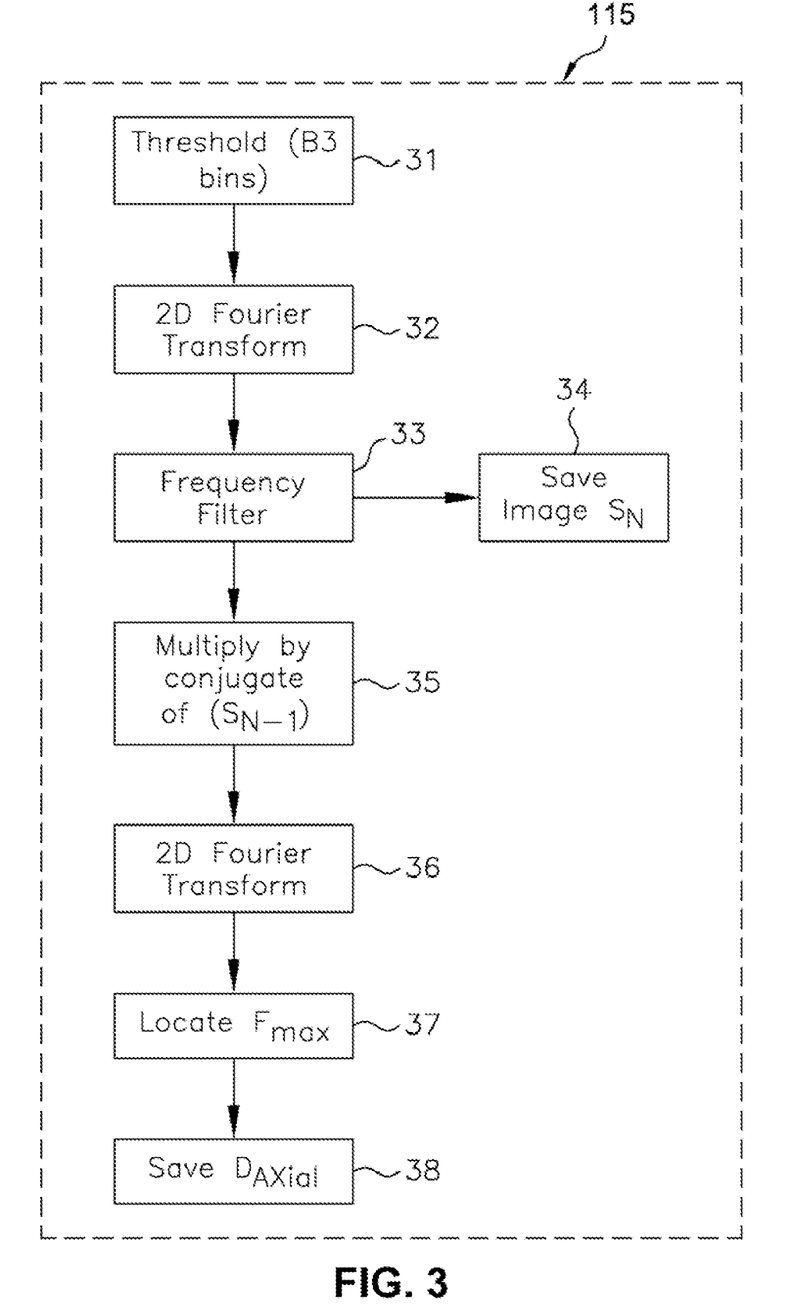
FIG. 3 is a functional block diagram of an axial correction portion of an imaging system employing the example embodiment described in FIG. 1.

Referring now to FIG. 3, a functional block diagram of an axial correction portion of an imaging system employing the example embodiment described in FIG. 1 is shown. The axial correction 115 is performed on all images except the first. A copy of the input image is thresholded at step 31, and then cross-correlated with a thresholded copy of the previous image. The offset is determined as the maximum in the cross-correlation function along the line that corresponds to the difference in the lateral correction for the current perspective [$D_{LAT}(N)$] and the lateral correction for the immediately preceding perspective [$D_{LAT}(N-1)$]. Unlike the lateral correction 114, therefore, the axial correction 115 is an iterative process and thus is subject to cumulative errors.

A copy of the input image is thresholded 31 in the same manner as for the lateral correction, but in this case the number of bins in the histogram is B3. In the present example, B3=2. Thus, all pixels with a gray level greater than the mid-range gray level are set to zero, while those with lower gray levels retain their initial values. For example, an input image with minimum and maximum values of 31 and 190, respectively, will result in a thresholded image identical to the initial one, except that all pixels that were initially brighter than 110 are now zero.

Having thus blacked out the bright pixels, the thresholded image is Fourier-transformed in 2D 32. It is then filtered 33 to eliminate the smallest features, which may produce spurious peaks on the cross correlation. Only spatial frequencies up to 102 cycles/pixel, corresponding to feature sizes of ten pixels or less, are multiplied and pixels at higher spatial frequencies are set to zero. The resulting array is saved 34 as $S_N$ and multiplied 35 by the complex conjugate of $S_{N-1}$, obtained from the preceding image's thresholded copy. A 2D FFT is next applied to the resulting array to find the cross-correlation of the two consecutive, thresholded, low-pass-filtered images. The difference in the lateral offset between the two consecutive images [$D_{LAT}(N)-D_{LAT}(N-1)$] found from the lateral correction step 114 is necessary now, since it is incorrect to find the global maximum of the correlation array. Instead, a local maximum, $F_{MAX}$, must be found in the row that corresponds to [$D_{LAT}(N)-D_{LAT}(N-1)$]. The column containing $F_{MAX}$ is designated $G_{MAX}$. If $G_{MAX}$ is greater than half the padded image dimension (1024, in this example), then its value signifies a negative shift, relative to the preceding image, having a magnitude equal to the zero-padded dimension minus the value of $G_{MAX}$. If $G_{MAX}$ is less than half the zero-padded dimension, then the required shift, relative to the preceding image, is positive and equal to $G_{MAX}$.

As an example, suppose $D_{LAT}(N-1)=45$, while $D_{LAT}(N)=63$. Then $F_{MAX}$ will be found on row 18 of the correlation array (63−45=18). If $F_{MAX}$, the maximum value of row 18, occurs in the fifth column, then $G_{MAX}=5$ and the image must be shifted five pixels to the left of the previous image. If the maximum occurs at row 1019 ($G_{MAX}=1019$), then the image must be shifted five pixels to the right (1024−1019=5) of the previous image, since 1019 is greater than 512.

After $G_{MAX}$ is found, the value of the shift is added to the sum of all the previous axial offsets to determine $D_{AXIAL}$, the cumulative difference from the first acquired image to the current image. The shift may be positive or negative; hence, some images may not require any axial shift. For each image, four values are written to a text file:

1. The position of the upper tube wall, $D_{LAT}$;
2. $C_{MAX}$, the maximum value of the cross-correlation between the current image and the reference image;
3. $G_{MAX}$, the location of $F_{MAX}$ on the appropriate row of the cross-correlation between the current image and the previous image (for the first image, $G_{MAX}=0$);
4. $F_{MAX}$ (for the first image, $F_{MAX}=0$).

The corrected file is generated by cropping the appropriate number of pixels from one or two edges and shifting the remaining pixels by the number cropped. To maintain the original image dimensions (640×480), the spaces at the opposite edges from the cropped edges are replaced by pixels set to the maximum gray level of the original image.

For example, suppose that for one of the images, the maximum gray level is 229, $D_{LAT}=63$, $D_{AXIAL}=29$, and $G_{MAX}=1022$. Then the pixels in the top eight rows (63−55=8) and the left 27 columns (29−1024+1022=27) are deleted from the image. Thus the ninth row of column 28 occupies the upper left corner. Eight rows are added to the bottom of the image, and 28 columns are added to the right of the image; these pixels have gray levels of 229. When these procedures are complete, the 632×453-pixel region in the upper left of the corrected image is identical to the 632×453-pixel region in the lower right of the original image. Both images have dimensions of 640×480.

Another example embodiment incorporates only the axial correction 115 and the writing of the corrected image 116. This embodiment is useful when the walls of the microcapillary tube are not visible and the tube's lateral motion is known to be negligible In yet another embodiment, the tube wall separation is calculated automatically from the first view (N=0). Otherwise it is identical to the embodiment described hereinabove with reference to FIGS. 1-3. In another embodiment of the invention, the separation of the tube walls is determined based on a calculation of their separation in one or more of the images. This is accomplished by using as a reference an image derived from a single bright line, as by a 2D FFT and a complex conjugation. The rows are summed, as in the first embodiment, and the location of the maximum is taken as the location of one wall of the tube relative to its location in the image from which the reference image was derived. The location of the next highest correlation value gives the location of the other tube wall, relative to the first. If desired, the search for this secondary maximum can be restricted to a range whose central location, relative to the first tube wall, is in the vicinity of the presumed tube width. This embodiment also encompasses the possibility of using the single-line reference for all the acquired viewpoints. Such an arrangement may be useful when the tube wall separation is not known, or when the tube's inner walls do not form a circle, as when the tube's inner profile is square is elliptical.

In another embodiment of the invention, the characteristics of the thresholding step may vary based on feedback from the correlation. Such iterative approaches may be employed in the first thresholding step for the lateral correction, in the second thresholding step for the axial correction, or in both. One characteristic that may be varied is the number of divisions or bins used in the histogram. Another characteristic that can be varied is the number of gray levels contained within each histogram bin. For example, the histogram may be based on the square root of the brightness level.

According to a feature of the invention, the output of the method is a cropped copy of the input file, with the uncropped portions shifted vertically and/or horizontally, and with additional blank pixels inserted at one or two of the borders to retain the input image size.

According to a further feature of the invention, the results of the method employed are saved to a digital file, which may be altered and edited using computer word-processing applications. The altered text file may then be used to generate the offsets in the two axes, thus bypassing many of the calculations described above. In this embodiment, the lateral correction procedure of steps 114 through 116 is iterated to find the maximum of $C_{MAX}$. If $C_{MAX}$ has a magnitude less than a critical value $C_{CRIT}$, then the entire procedure is repeated, starting with the thresholding 27, but with the number of bins in the histogram changed from B1 to B2. $C_{MAX}$ is again located 26 and evaluated 28.

Figure 5:
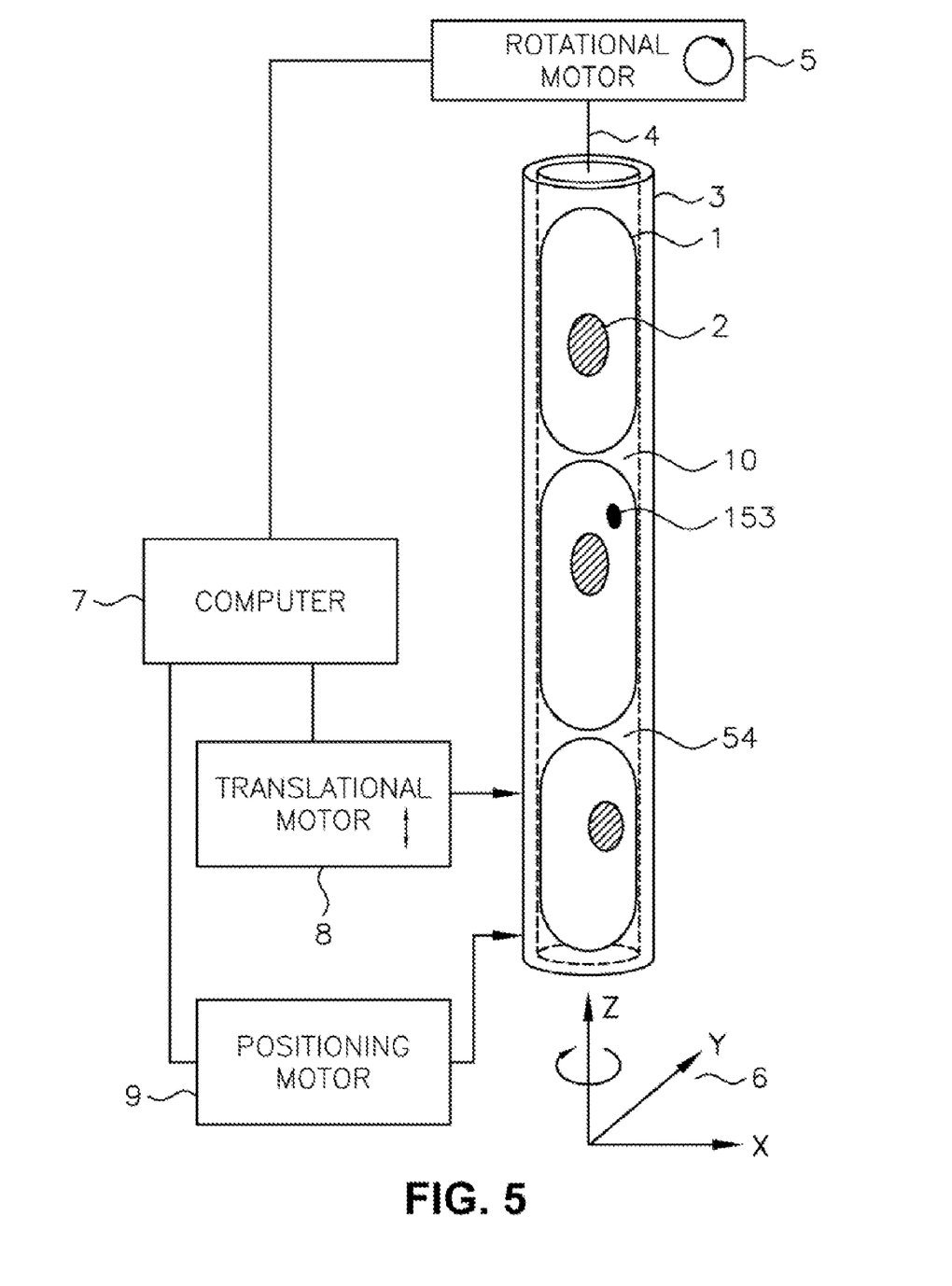
FIG. 5 depicts schematically an optical projection tomographic microscopy (OPTM) system employed in one embodiment of the invention.

Referring now to FIG. 5, there shown schematically is an example illustration of cells packed into a capillary tube as contemplated by an embodiment of the present invention. In this example embodiment, a section of the capillary tube 3 is filled with objects of interest 1, such as cells, that are packed rigidly into the tube. Each of the cells may include a nucleus 2. The capillary tube 3 has a central axis 4 oriented with reference to a coordinate system 6 having coordinates in the x, y and z-directions. In some instances, at least one molecular probe 153 may be bound within the cell. A computer 7 is coupled to provide control signals to a rotational motor 5 and a translational motor 8. It will be recognized that equivalent arrangements of one or more motors, gears or fluidics or other means of generating motion may also be employed to achieve the necessary translational and rotational motion of the capillary tube or other substrate. In some cases, one or more of the motors may be replaced by manual positioning devices or gears or by other means of generating motion such as hydraulic or piezoelectric devices. The axis of translation is the z-axis, and rotation is around the z-axis. The positioning motor 9 is coupled to move the cell in a plane defined by the x, y-axes, substantially perpendicular to the central axis for the purpose of centration, as necessary.

It will be recognized that the curved surface of the capillary tube will act as a cylindrical lens and that this focusing effect may not be desirable in a projection system. Those skilled in the art will appreciate that the bending of photons by the tube can be eliminated if the spaces between the point source and the tube and between the tube and the detector surfaces are filled with a material 10 whose index of refraction matches that of the capillary tube and that the tube can be optically coupled (with oil or a gel, for example) to the space filling material.

Consider the present example of cells packed into a capillary tube. The cells may preferably be packed single file so that they do not overlap. The density of packing whole cells of about 100 microns in diameter into a capillary tube with diameter less than 100 microns can be roughly 100 cells per centimeter of tube length. For bare nuclei of about 20 microns in diameter, the packing can be roughly 500 nuclei per centimeter of tube length where the tube diameter is proportional to the object size, about 20 microns in this case. Thus, within several centimeters of capillary tube length, a few thousand non-overlapping bare nuclei can be packed. By translating the tube along its central axis 4, motion in the z-direction can be achieved. Moving the tube in the x,y-directions allows objects within the tube to be centered, as necessary, in the reconstruction cylinder of the optical tomography system. By rotating the tube around its central axis 4, a multiplicity of radial projection views can be produced. Moving the tube in the z-direction with constant velocity and no rotation simulates the special case of the flow optical tomography.

One advantage of moving a tube filled with cells that are otherwise stationary inside the tube is that objects of interest can be stopped, then rotated, at speeds that permit nearly optimal exposure for optical tomography on a cell-by-cell basis. That is, the signal to noise ratio of the projection images can be improved to produce better images than may be usually produced at constant speeds and direction typical of flow systems. Objects that are not of interest can be moved out of the imaging systems swiftly, so as to gain overall speed in analyzing cells of interest in a sample consisting of a multitude of cells. Additionally, the ability to stop on an object of interest, then rotate as needed for multiple projections, nearly eliminates motion artifacts. Still further, the motion system can be guided at submicron movements and can advantageously be applied in a manner that allows sampling of the cell at a resolution finer than that afforded by the pixel size of the detector. More particularly, the Nyquist sampling factor of 2 could be managed by the motion system moving in increments that fill half a pixel width, for example. Similarly, the motion system can compensate for the imperfect fill factor of the detector.

Figure 6A:
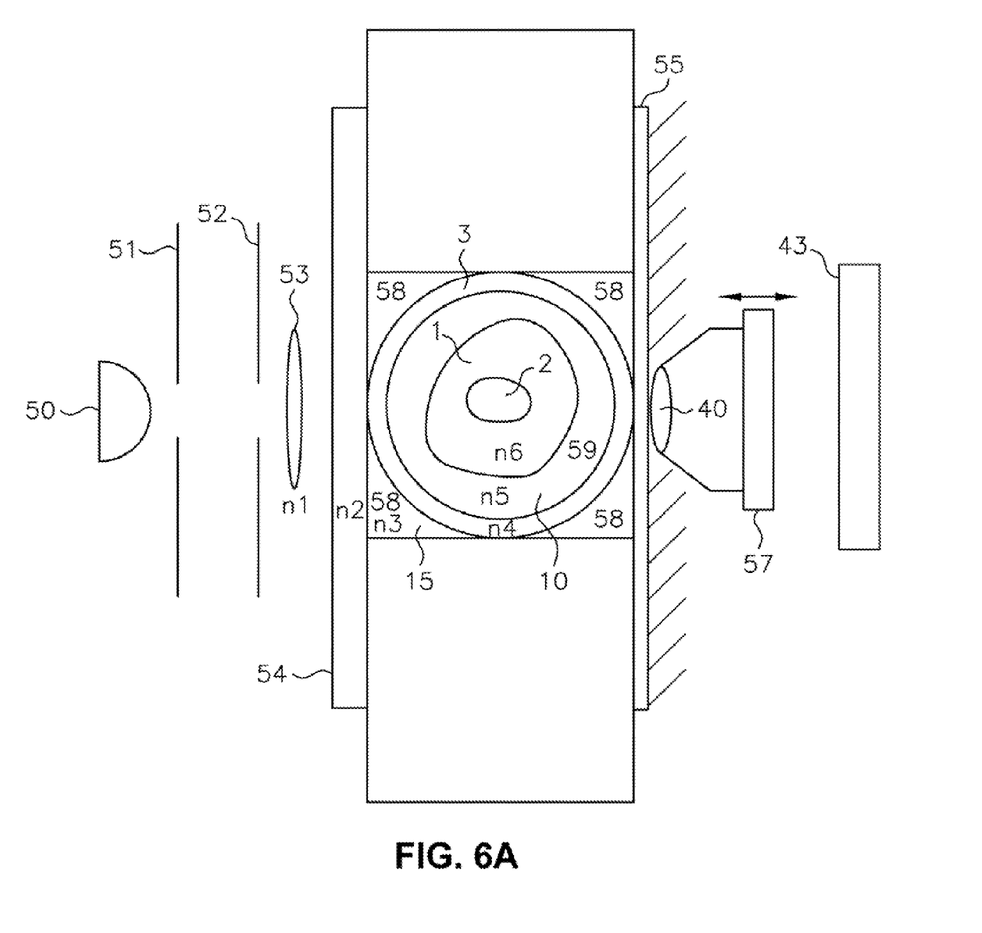
FIG. 6A and FIG. 6B show one embodiment of an optical tomography system incorporating a microscope objective lens mounted on a piezoelectric translation device is schematically shown.

Referring now to FIG. 6A, there shown is a close-up view of a single specimen, as for example a single cell, immersed within a medium of optical indexing material. The single specimen is shown within a micro-capillary tube 3 (e.g. one such tube is manufactured by Polymicro Technologies, LLC., AZ, US) that can be rotated for taking multiple projections and an objective lens 40 that can be axially scanned is schematically shown. An illumination source includes a light source 50 that projects light through an aperture 51, a stop 52, and through a condenser lens 53 that is positioned before a microscope slide 54. A micro-capillary tube 3 holds a cell 1 between the slide and a thin coverslip 55. An objective lens 40, preferably an oil-immersion lens, is disposed to receive light passed through the micro-capillary tube 3. The objective lens is translated along the optical axis by an actuator 57 such as a piezoelectric element. The coverslip 55 must be thin enough so that the distance between the center of the micro-capillary tube and the outer surface of the coverslip is smaller than the working distance of the objective lens. The condenser lens 53 is within the index of refraction $n_1$ (e.g. air). The slide 54 and coverslip 55 have index of refraction $n_2$. A region 58 surrounding the micro-capillary tube 3 contains index-matching medium 15 such as optical gel or immersion oil, which has index of refraction $n_3$. The micro-capillary tube 3 itself has index of refraction $n_4$. The region 59 surrounding the cell 1 within the micro-capillary tube contains a medium 10 possessing an index of refraction $n_5$. A region 60 within the cell may be filled with the same medium 10, or may differ in its index of refraction $n_6$. It is preferred that $n_3=n_4=n_5=n_6$ (differences must be minimized) between the two flat parallel surfaces formed by slide 54 and coverslip 55 to avoid a cylindrical lens distortion. The image is projected onto a camera 43.

Figure 6B:
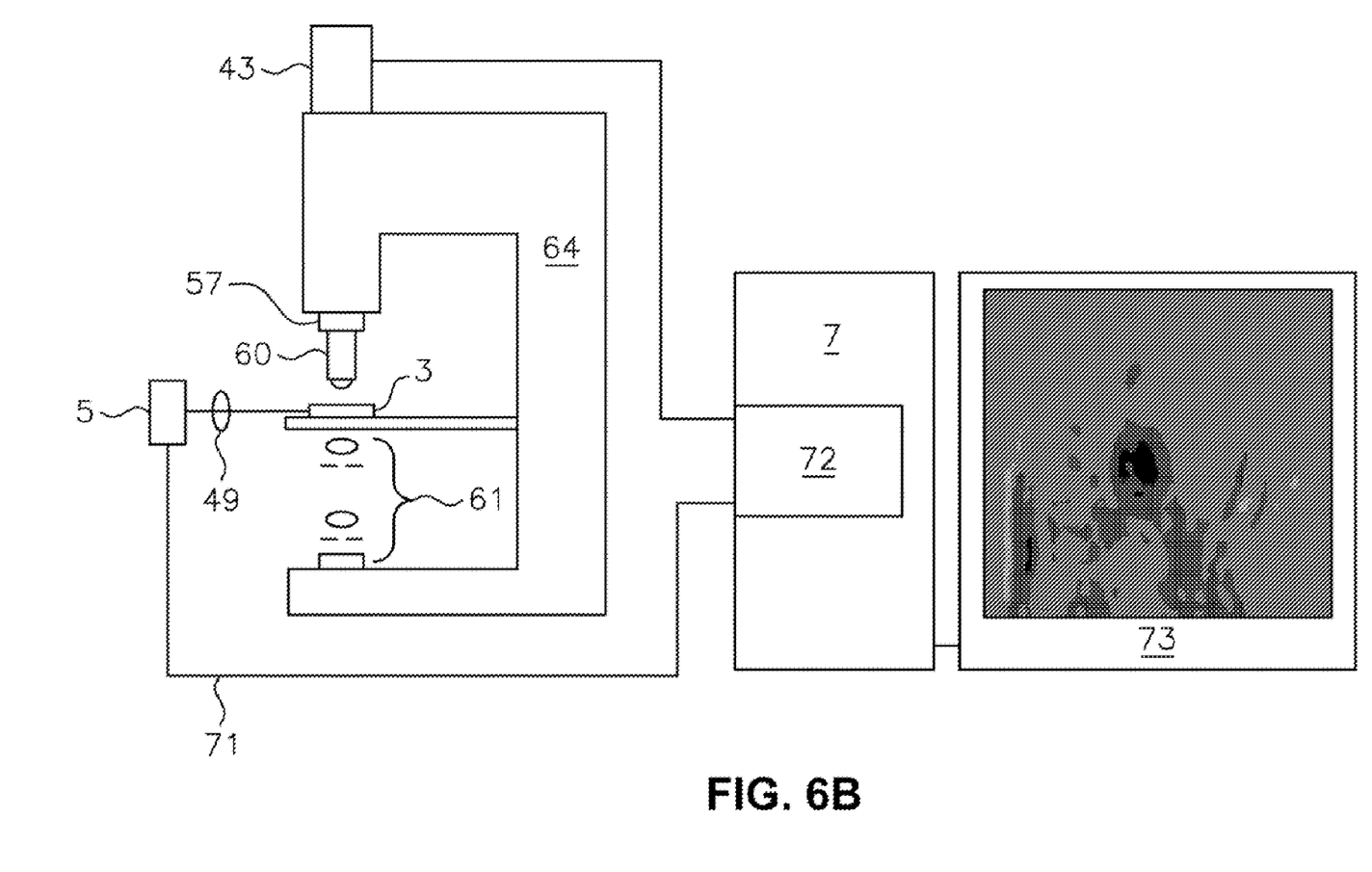

Referring now to FIG. 6A and FIG. 6B, one embodiment of an optical tomography system employed in the present invention, incorporating a microscope objective lens mounted on a piezoelectric translation device is schematically shown. The piezoelectric transducer 57 is used to move an objective lens 60 an axial distance of about 40 microns or more. In one useful embodiment, a micro-objective positioning system provides a suitable actuator 57, which is driven up and down along the z axis of tube coordinate system 6. In this embodiment, it may be used with a high numerical aperture objective, mounted on an standard transmission microscope 64 with a video camera 43 attached and a computer-controlled light source and condenser lens assembly 61. The computer-controlled condenser and light source 50 may advantageously be a light source including one or more incandescent bulbs, an arc lamp, a laser, or a light emitting diode. Computer control signals 70 are linked to the computer-controlled condenser and light source 50 for controlling light modulation.

The output from the camera 43 is stored in a computer memory 72. A microcapillary tube 3 containing the specimen can be translated along the x or y axes of tube coordinate system 6. In addition, the microcapillary tube 3 can be rotated about its "θ" axis 49, via a rotational motor 5 that can be computer-controlled. As used herein micro-capillary tube is defined as a capillary tube having a diameter where the field of view for microscopic imaging is comparable to the capillary tube diameter. In an example embodiment the rotational motor 5 is controlled by control signals 71 as provided by the computer 7. For high speed applications other controls may be added in order to reduce vibrations during an axial scan. The acquired image may be displayed on monitor 73.

Figure 7:
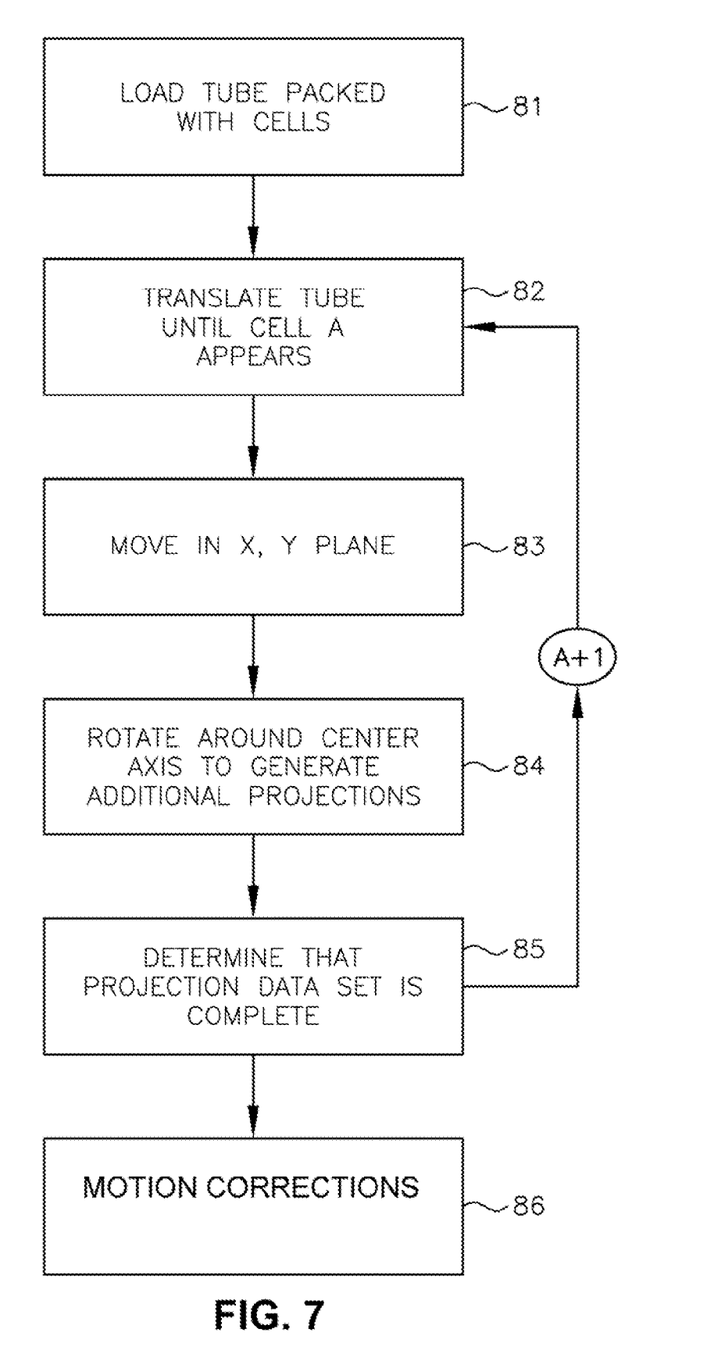
FIG. 7 shows an example flow diagram illustrating a process for acquiring images used in three-dimensional (3D) image reconstruction as contemplated by an embodiment of the present invention.

Referring now to FIG. 7, an example flow diagram illustrating a process for acquiring images used in three-dimensional (3D) image reconstruction as contemplated by an embodiment of the present invention is shown. As contemplated by one example of the present invention, a 3D image reconstruction process includes the steps of loading the tube packed with cells at step 81, translating the tube until the first cell of interest has been located at step 82, centering the cell of interest, as necessary, at step 83, generating a set of projections at each different rotation angle at step 84, determining when the data set is complete at step 85, and repeating the process from steps 82 through 85 until all cells of interest have been scanned. At step 86 registration corrections are made. The process may be implemented in a computer software program executed by a personal computer such as computer 7, for example.

Figure 8:
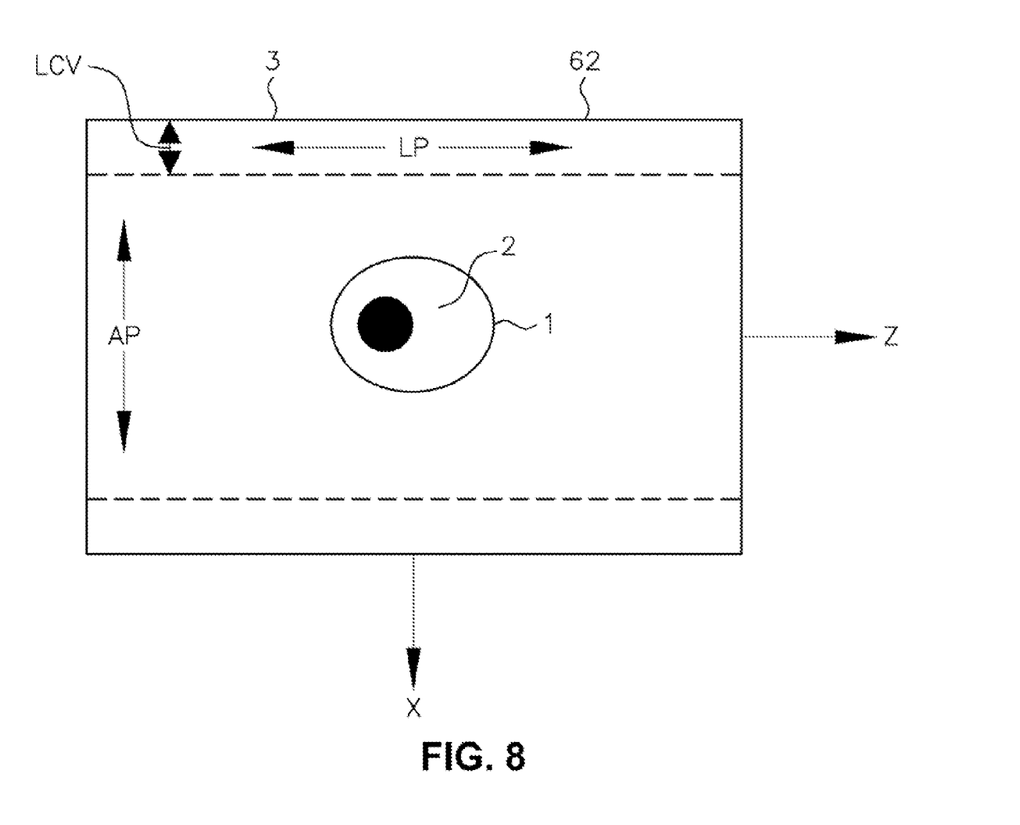
FIG. 8 shows schematically an example of registration correction offsets for use in a three-dimensional (3D) image reconstruction as contemplated by an embodiment of the present invention.

Referring now to FIG. 8, there shown schematically is an example of registration correction offsets for use in a three-dimensional (3D) image reconstruction as contemplated by an embodiment of the present invention. Registration correction is applied to find the lateral position of an object of interest 1, such as a cell or nucleus 2, contained in a capillary tube 3 having a capillary tube wall 62. The lateral offset is the error along the longer image dimension (640 pixels), perpendicular to the tube axis, Z. The axial offset is the error along the shorter image dimension (480 pixels), parallel to the tube axis Z. The object of interest 1 has a lateral position LP and an axial position AP. As images are acquired from various points of view, registration correction is applied in order to allow reconstruction of the object of interest with identical features maintained in the same plane in the various views.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. Apparatus for correcting positioning and motion errors in an imaging system, comprising:
    means for acquiring and electronically storing at least two consecutive views of an object in a tube, said at least two views including M rows and N columns of image brightness data;
    a first producing means for producing a first set of modified copies of each of said at least two consecutive views by applying an alteration of brightness level to pixels having brightness levels within a specified range;
    a first cross-correlation means for performing a cross-correlation between said first set of modified copies with a reference pattern to produce a first cross-correlated array;
    a first locating means for locating and evaluating a maximum of the first cross-correlated array, where a location of said maximum determines the value of a coefficient "A";
    a second producing means for producing a second set of modified copies of each of said at least two consecutive views by applying an alteration of brightness level to pixels having brightness levels within a specified range;
    a second cross-correlation means for performing a second cross-correlation between two of said set of modified copies to produce a second cross-correlation array;
    a second locating means for locating and evaluating a restricted maximum of the second cross-correlation array, said restriction being that the row or column on which said restricted maximum is located must be orthogonal to and intersect the row or column on which coefficient "A" is located, the location of said restricted maximum determining a coefficient "B;" and
    a motion-corrected image means for producing a motion-corrected image by shifting at least one of said at least two consecutive views by values determined by coefficient "A," and coefficient "B," wherein the reference pattern comprises a binary template representing the structure of the tube.

2. Apparatus according to claim 1, wherein the motion-corrected image means operates responsively to said values of said coefficients "A" and "B" for shifting one of the at least two consecutive views in two orthogonal directions relative to the other of the at least two consecutive views.

3. Apparatus according to claim 1, in which the first cross-correlating means includes a means for summing a selected one of the M rows and N columns to obtain a one-dimensional array, said summing being in a direction orthogonal to the direction of the shift whose magnitude is determined by said coefficient "A."

4. Apparatus according to claim 1 in which the reference pattern comprises an array of M rows and N columns of image brightness data in which all pixels can have only one of two possible brightness values.

5. Apparatus according to claim 1 wherein the reference pattern comprises an array of M rows and N colonels of image brightness data in which all pixels have the same brightness value, with the exception of two groups consisting of one or more rows or columns, said two groups having a brightness that is uniform, but different than the other pixels, and having a separation that corresponds to the separation of opposing walls of a microcapillary tube, said opposing walls both appearing in the field of view of a succession of two or more images, said microcapillary tube containing an object of interest.

6. Apparatus according to claim 5 in which the object of interest comprises an object selected from the group consisting of a biological cell and a biological nucleus.

7. Apparatus according to claim 1 including means for finding a maximum value of a maximum correlation based on multiple thresholding.

8. Apparatus according to claim 5 including means for computing separation of at least one of two groups, rows and columns using at least one acquired image.

9. A method for three dimensional (3D) reconstruction of an object of interest, comprising the steps of: using a processor to perform steps comprising:
    (a) packing a set of objects of interest into a tube;
    (b) illuminating at least one object of the set of objects of interest with at least one optical projection beam;
    (c) translating the tube until the at least one object of interest is located within a region of the at least one optical projection beam;
    (d) rotating the at least one object through a plurality of perspectives;
    (e) generating an image at each perspective to produce a set of images;
    (f) correcting registration of the set of images of the at least one object of interest by determining a lateral offset correction value for each image, determining an axial offset correction value for each image, and applying the lateral offset correction value and the axial offset correction value to each image to produce a set of motion-corrected images; and
    (g) wherein the method of determining an axial offset correction value for each image includes producing a first set of modified copies of the set of images in which an alteration of brightness level is applied to pixels having brightness levels within a specified range, performing a first cross-correlation between the first set of modified copies and a reference pattern to produce a first cross-correlation array, locating and evaluating a maximum of the first cross-correlation array and performing a second cross-correlation between said first set of modified copies and said reference pattern to determine the value of a coefficient "A", producing a second set of modified copies of the set of images in which an alteration of brightness level is applied to pixels having brightness levels within a specified range, performing a third cross-correlation between the second set of modified copies to produce a second cross-correlation array, and locating and evaluating the restricted maximum of the second cross-correlation array, said restriction being that the row or column on which said restricted maximum is located must be orthogonal to and intersect the row or column on which coefficient "A" is located, the location of said restricted maximum determining a coefficient "B," wherein the reference pattern comprises a binary template representing the structure of the tube.

10. The method of claim 9, wherein the at least one object comprises an object selected from the group consisting of a biological cell and a cell nucleus.

11. The method of claim 9, wherein the reference pattern of image brightness data comprises a reference image generated from a different perspective than modified copies being correlated with the reference image.

12. The method of claim 9, wherein the reference pattern of image brightness data comprises a modified reference image, where an alteration of brightness level is applied to pixels in the reference pattern having brightness levels within a specified range to create the modified reference image.

13. The method of claim 9, wherein the reference pattern of image brightness data comprises a selected one of a modified and unmodified representation of a microcapillary tube.

14. A method for three dimensional (3D) reconstruction of an object of interest, comprising the steps of: using a processor to perform steps comprising:
   (a) packing a set of objects of interest into a tube;
   (b) illuminating at least one object of the set of objects of interest with at least one optical projection beam;
   (c) translating the tube until the at least one object of interest is located within a region of the at least one optical projection beam;
   (d) rotating the at least one object through a plurality of perspectives;
   (e) generating an image at each perspective to produce a set of images;
   (f) correcting registration of the set of images of the at least one object of interest by determining a lateral offset correction value for each image, wherein the method of determining a lateral offset correction value for each image comprises the steps of:
      (i) prior to the application of any reconstruction techniques, producing a modified copy of each of the set of images in which an alteration of brightness level is applied to pixels having brightness levels within a specified range;
      (ii) performing a cross-correlation between said modified copy of said view with a reference pattern to produce a cross-correlated array; and
      (iii) locating and evaluating a maximum of the cross-correlated array; and
   (g) applying the lateral offset correction value to each image to produce a set of lateral-motion-corrected images, wherein the reference pattern comprises a binary template representing the structure of the tube.

15. The method of claim 14, wherein the at least one object comprises an object selected from the group consisting of a biological cell and a cell nucleus.

16. The method of claim 14, wherein the reference pattern of image brightness data comprises a selected one of a modified and unmodified representation of a microcapillary tube.

* * * * *